(12) United States Patent
Muizzuddin et al.

(10) Patent No.: US 6,680,062 B2
(45) Date of Patent: Jan. 20, 2004

(54) ANTI-IRRITATING ROSACEA TREATMENT

(75) Inventors: Neelam Muizzuddin, Bethpage, NY (US); Kenneth D. Marenus, Dix Hills, NY (US); Daniel H. Maes, Huntington, NY (US)

(73) Assignee: Color Access, Inc., Melville, NY (US)

( * ) Notice: Subject to any disclaimer, the term of this patent is extended or adjusted under 35 U.S.C. 154(b) by 215 days.

(21) Appl. No.: 09/971,561

(22) Filed: Oct. 5, 2001

(65) Prior Publication Data

US 2003/0068343 A1 Apr. 10, 2003

(51) Int. Cl.$^7$ .............................. A61K 6/00; A61K 7/00; A61K 35/80; A61K 35/78; A01N 65/00
(52) U.S. Cl. .................. 424/401; 424/195.17; 424/729; 514/159; 514/887
(58) Field of Search ................................. 424/401, 405, 424/70.1, 70.8, 70.13, 195.17, 729; 514/548, 887, 520, 159

(56) References Cited

U.S. PATENT DOCUMENTS

| | | | |
|---|---|---|---|
| 5,089,481 A | 2/1992 | Muto et al. | 514/54 |
| 5,306,486 A | 4/1994 | McCook et al. | 424/59 |
| 5,624,911 A | 4/1997 | Fenical et al. | 514/33 |
| 5,728,732 A | 3/1998 | Corey et al. | 514/544 |
| 5,792,794 A | 8/1998 | Lambers et al. | 514/559 |
| 5,811,114 A | 9/1998 | Knight et al. | 424/408 |
| 5,885,595 A | 3/1999 | Corey et al. | 424/401 |
| 5,932,215 A | 8/1999 | de Lacharriere et al. | 424/158.1 |
| 5,952,372 A | 9/1999 | McDaniel | 514/453 |
| 5,972,993 A | 10/1999 | Ptchelintsev | 514/449 |
| 6,153,208 A | * 11/2000 | McAtee et al. | 424/401 |

FOREIGN PATENT DOCUMENTS

| | | |
|---|---|---|
| WO | 97/00689 | 1/1997 |
| WO | 99/29293 | 6/1999 |
| WO | 00/01839 | 1/2000 |

OTHER PUBLICATIONS

Wilkin, J. K., M.D., et al., "Infrared Photographic Studies of Rosacea", Arch Dermatol, vol. 116, pp. 676–678 (1980).
Pye, R. J., et al., "Skin Surface Lipid Composition in Rosacea", British Journal of Dermatology, vol. 94, pp. 161–164 (1976).
Signore, R. J., "A Pilot Study of 5 Percent Permethrin Cream Versus 0.75 Percent Metronidazole Gel in Acne Rosacea", CUTIS vol. 56, pp. 177–179 (1995).
Guarrera, M., et al., "Flushing in Rosacea: A Possible Mechanism", Arch Dermatol Res, vol. 272, pp. 311–316 (1982).
Plewig, G. and Kligman, A. M., "Acne and Rosacea", title page, pp. 431–475, Springer–Verlag (2d ed. 1993.
Jensen, P. R., et al., "Antimicrobial Activity of Extracts of Caribbean Gorgonian Corals", Marine Biology, vol. 125, Springer–Verlag (1996) (abstract).
Database JAPIO on Dialog, JP 2000–109409A (Taketoshi et al.), Abstract.

* cited by examiner

*Primary Examiner*—Sreeni Padmanabhan
*Assistant Examiner*—Lauren Q. Wells
(74) *Attorney, Agent, or Firm*—Dorene M. Price, Esq.

(57) ABSTRACT

The present invention relates to a cosmetic or pharmaceutical composition for topical application to the skin afflicted with rosacea and treated with a retinoid. The composition for treating rosacea comprises an anti-irritating component and several other components for treating rosacea. The other components form a mixture of a salicylic acid, a phytosphingosine, green tea, hinokitiol, gorgonian extract, and polysaccharide. The invention also provides a method for decreasing the irritation on the skin caused by the heightened sensitivity experienced by skin suffering from rosacea. The other components are effective in treating the rosacea condition, but particularly, in treating the telangiectasic symptom of rosacea.

10 Claims, 1 Drawing Sheet

US 6,680,062 B2

ANTI-IRRITATING ROSACEA TREATMENT

FIELD OF THE INVENTION

The invention relates to topically applied cosmetic and pharmaceutical compositions which treat rosacea. In particular, the invention relates to cosmetic and pharmaceutical compositions containing a mixture of components which are substantially non-irritating to the skin when used to treat rosacea.

BACKGROUND OF THE INVENTION

Rosacea is a common skin condition characterized by symptoms of flushing episodes, erythema, telangiectasia, and the recurring presence of inflammatory papules and pustules on the face usually arranged in a symmetrical distribution across the cheeks and the nose. Fair skinned people are more likely to experience and suffer from rosacea. It is believed that, in general, patients with rosacea have skin that is oily, thin, and has a high microflora count. While many of the effects of rosacea are skin related, rosacea can cause emotional damage because physically it can appear socially unsightly to patently disfiguring. Therefore, any improvement in the treatment of rosacea can have an enormous effect on the lives of those who suffer from this condition.

As a result of flushing and telangiectasia, the facial skin of rosacea sufferers is typically ruddy. The color change observed with rosacea is concentrated in certain areas of the face. It is theorized that the color change associated with rosacea is a result of the dilation of nonmuscular endothelial capillaries and venules. Wilkin, J. K., M.D., et al., "Infrared Photographic Studies of Rosacea", Arch Dermatol, vol. 116, pp. 676–678 (1980). Provocative factors which trigger the onset of symptoms are well known. These factors include vasodilating stimuli, alcoholic beverages, exposure to heat and sunlight, and *Demodex folliculorum.*

Unlike its symptoms and triggers which are well known, the pathology of rosacea remains elusive. One theory is that rosacea is clinically similar to acne vulgaris, and is frequently, therefore, referred to as acne rosacea. Like acne, rosacea exhibits characteristics of sebaceous gland hyperplasi in rhinophyma. However, studies have been conducted to disprove this theory. For example, the skin surface lipid composition of patients with rosacea has shown that the skin surface lipid composition is normal in rosacea and there is no indication of a decrease in free fatty acids when the skin is subjected to a tetracycline treatment regimen. Therefore, it is concluded that changes in free fatty acid levels cannot be implicated in the pathogenesis of rosacea. It is further concluded that rosacea is not primarily a disorder of the pilosebaceous apparatus, Pye, R. J., et al., "Skin Surface Lipid Composition in Rosacea", British Journal of Dermatology, vol. 94, pp. 161–164 (1976), and thus, it is believed that the processes of acne and rosacea are separate and distinct.

Flushing and the regulatory mechanism of the blood vessels are of importance in the pathogenesis of rosacea. The stages associated with flushing progress from episodes of flushing to persistent telangiectases. Telangiectasia, the dilation of capillaries and small blood vessels, has been studied using infrared photography and results have indicated, consistent with a previously developed theory, that the color change in rosacea is due to the dilation of the nonmuscular endothelial capillaries and venules.

Treatment for rosacea can be orally or topically applied antibiotics, such as tetracycline, clindamycin, erythromycin, as well as vitamin A, salicylic acid, zinc oxide, antifungal agents, or steroids. Another known treatment for rosacea is metronidazole (an antiprotozoal and antibacterial agent) and permethrin (a pyrethroid), alone or with oral 13-cis-retinoic acid (isotretinoin). Signore, R. J., "A Pilot Study of 5 Percent Permethrin Cream Versus 0.75 Percent Metronidazole Gel in Acne Rosacea", CUTIS, vol. 56, pp. 177–179 (1995). Metronidazole, however, has been reported as ineffective against skin redness, telangiectases and flushing.

Drugs for inhibiting flushing include, for example, methysergide, indomethacin, clonidine, aspirin, promethazine, propranolol, diazepam, and cimetidine. Guarrera, M., et al., "Flushing in Rosacea: A Possible Mechanism", Arch Dermatol Res, vol. 272, pp. 311–316 (1982). In addition, U.S. Pat. No. 5,952,372 discloses a method of treating rosacea with oral or topical use of ivermectin, and U.S. Pat. No. 5,932,215 discloses the use of Calcitonin Gene Related Peptide (CGRP), a substance P antagonist, in compositions to treat skin redness in discrete erythema and rosacea. However, the treatment of the present invention is an improvement over these prior art treatments because known treatments for flushing either do not address other aspects of rosacea such as papules and pustules or are irritating to the sensitive skin of the rosacea sufferer.

It is frequent to find that the skin suffering from rosacea is hypersensitive, and therefore, the treatment for rosacea is or feels particularly irritating to the skin. In fact, most patients with rosacea complain of sensitive skin that stings, burns, and itches after application of treatment compositions, cosmetics, fragrances, or sunscreens because their facial skin is unusually vulnerable to chemical and physical stimuli. Plewig, G. and Kligman, A. M., "Acne and Rosacea", p. 435 (2d ed. 1993) (hereinafter "Acne and Rosacea"). Soaps, alcoholic cleansers, tinctures and astringents, abrasives and peeling agents are all potential irritants and should be avoided. Therefore, reducing irritation associated with compositions designed to treat rosacea is a special problem. Even more difficult to treat, is the irritation experienced when treating the skin for rosacea complexed with acne vulgaris. Typically products are formulated to be free of irritating ingredients such as actives, surfactants emulsifiers, and fragrances. When this approach is taken, there can be a compromise in the efficacy of the ingredients with respect to their desired activity. It has now been surprisingly discovered, as the foregoing discussion shows, that effective ingredients for treating rosacea, which typically would expect to be or feel irritating to the sensitive skin of rosacea, can be used with not only substantially no irritation, but with a pleasant feel that glides elegantly on the skin.

SUMMARY OF THE INVENTION

The present invention relates to cosmetic and pharmaceutical compositions for topical application to skin treated with a retinoid for a condition of rosacea comprising, a phytosphingosine, an antioxidant component comprising at least green tea, an anti-bacterial component comprising at least hinokitiol and a salicylate, and an anti-irritating component comprising at least a polysaccharide and gorgonian extract. The compositions of the present invention are capable of treating the symptoms of rosacea, especially the symptoms related to telangiectasia, such as flushing, while also being substantially non-irritating. The treatment of rosacea is enhanced, and the potential irritation felt on the skin using the retinoid for rosacea treatment is minimized by a combination of the phytosphingosine, the antioxidant component comprising at least green tea, an anti-bacterial component comprising at least hinokitiol and the salicylate, and an anti-irritant component comprising at least a polysaccharide, a gorgonian extract component.

Other features of the present invention are the methods associated with the topical application of the substantially non-irritating rosacea treatment of the present invention. In particular, the present invention includes the method of decreasing the irritation of skin associated with rosacea treatment regimen of topically applied retinoid, the method of treating telangiectasia with phytosphingosine, and therefore, it also includes the method of reducing redness associated with the appearance of rosacea. The present invention is particularly beneficial when used in conjunction with rosacea treatments of topically applied retinoids.

DETAILED DESCRIPTION OF THE INVENTION

Figure 1:
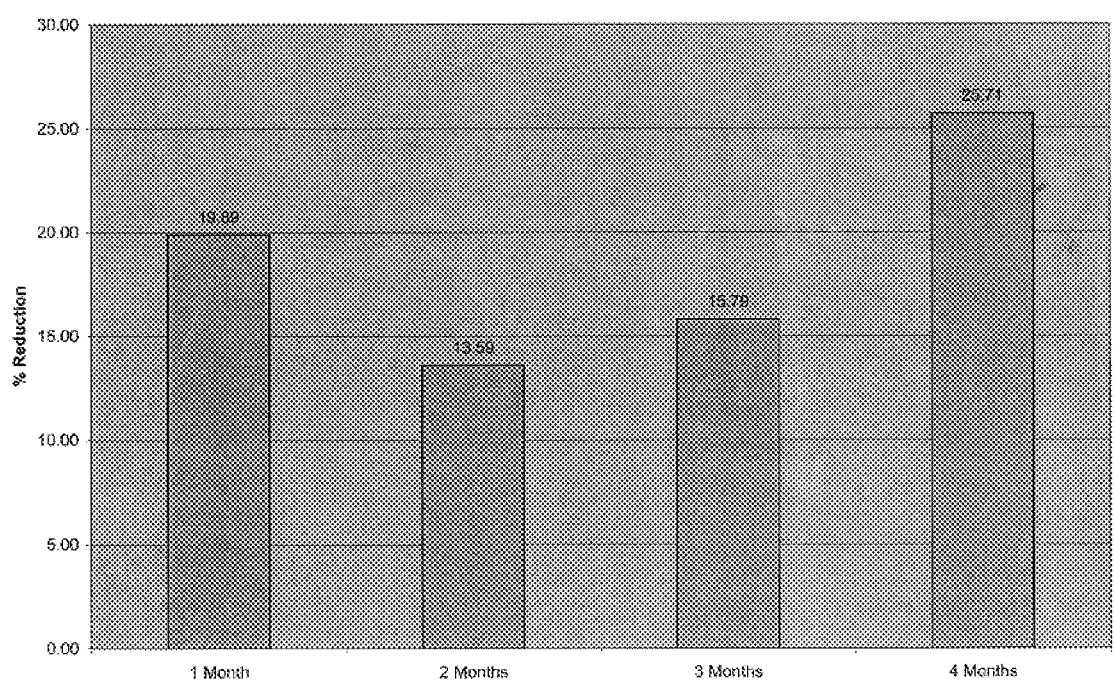
FIG. 1 is a chart illustrating the effect of the present invention in reducing the redness associated with flushing by measuring the percent reduction of blood flow in facial skin at intervals of one, two, three, and four months.

The rosacea treatment of the present invention is effective on skin treated with a retinoid for the rosacea condition. As previously mentioned, retinoids have proven useful in the treatment of acne rosacea. However, irritation can be experienced when using retinol to treat rosacea because of the heightened sensitivity of the facial skin suffering from rosacea. An unsaturated retinol fatty acid ester has been described in U.S. Pat. No. 5,885,595 whereby rosacea can be treated with less irritation. However, the present formulations succeed in reducing the irritation typically associated with rosacea treatment using different types of retinoids. Therefore, the rosacea sufferer can choose from a variety of retinol treatment regimens. The retinoid used to treat rosacea can be retinol (Vitamin A) and any of its derivatives, such as for example, retinyl palmitate, retinal, retinyl acetate, retinoic acid, and the like. The retinoid is used in an amount sufficient to effectively treat the symptoms of rosacea in combination with the other components of the present invention. The retinoid can be incorporated in the compositions of the present invention or be part of a separate treatment. However, preferably, the application of retinoids is part of a separate topical rosacea treatment regimen. The specific amounts of the retinoid can be, for example, about 0.001 to 5.00 percent, more preferably about 0.01 to 2.00 percent, concentration by weight of the total composition for rosacea treatment.

The compositions of the present invention include a cocktail of ingredients especially designed to alleviate the irritation experienced when treating rosacea, especially with a retinoid. Further, it has been surprisingly found that the inclusion of a phytosphingosine with the other active ingredients of the present invention, improves the condition of telangiectasia associated with rosacea. Although redness occurs with an inflammatory response or a deranged regulation of cell growth and differentiation of keratinocytes, the redness due to telangiectasia is vascular, and therefore, treatment for redness due to an inflammatory response will not necessarily treat redness due to vascular dilation, and most likely will not at all. Thus, the treatment of redness associated with rosacea, even when the skin is being treated for rosacea which can further irritate the skin, with the phytosphingosine and the other components of the present invention is unexpected. Some of the other active agents in the rosacea treatments of the present invention have been previously used in the treatment of rosacea. However, they have not been previously used with the phytosphingosine or collectively with one another as they are in the present invention to reduce irritation associated with a retinoid-containing rosacea treatment.

The phytosphingosine component is also known as an added active ingredient in cosmetic and pharmaceutical compositions, as explained in WO 00/01839 and in WO 99/29293, for their anti-inflammatory and antimicrobial activity, and as described in JP 2000109409, a phosphate of sphingosine for use in preventing acne. The contents of these references are incorporated herein. However, WO 00/01839 describes an enhanced method of producing sphingoid bases and derivatives such as phytosphingosines and, WO 99/29293 teaches a combination of a ceramide and a free sphingoid base which, when topically applied, allegedly benefit bacterial, fungal, yeast and viral infections, including rosacea. It has been taught in U.S. Pat. No. 5,792,794, also incorporated herein by reference, that coupling-products of retinoic acid or analogues with sphingoid bases such as phytosphingosines were stable and lacked irritating qualities similar to retinol derivatives retinyl-acetate and -palmitate. The compound is a sphingoid base linked through an amide to a retinoic acid. However, it has not been taught that the phytosphingoid by itself, or the other components of the present invention in simple admixture with a phytosphingoid (i.e., as separate components) can be substantially nonirritating especially when used in conjunction with a retinoid treatment for rosacea, nor has it been taught that a phytosphingoid by itself, or in combination with the other components, has any inherent effect on telangiectasia through anti-angiogenesis activity.

The effect of phytosphingosine in the present invention for treating telangiectasia is measured by the reduction of the flow of blood in facial skin. As shown in FIG. 1, the phytosphingosine acts in combination with the other components of the present invention as a vasoconstrictor. After four months of treatment, blood flow to the facial skin is reduced by about 25 percent. In addition, the presence of phytosphingosine also contributes to other known benefits such as treating acne comedones, serving as a building block for new ceramides, inducing de novo biosynthesis of ceramides, and acting as an important physiological regulator of growth and differentiation of epidermal cells as described in U.S. Pat. No. 5,792,794. The amount of the phytosphingosine used in the present invention for treating telangiectasia is from about 0.01 to about 10.0 percent by weight of the composition. Preferably, the amount of phytosphingosine is about 0.5 to 5.0 percent. The phytosphingosine of the present invention is available commercially from Gist-Brocades, Netherlands.

One of the other components of the present invention is the anti-bacterial component which comprises at least a salicylate and a hinokitiol. As used in the present specification, salicylates, known for treating skin microflora, can be, for example, salicylic acid, a common component of cosmetic and pharmaceutical compositions, and other salicylic acid esters. Preferably, the salicylate is a salicylic acid. However, currently available salicylic acid treatments are typically aggressive and too harsh for the skin plagued with rosacea as disclosed in U.S. Pat. No. 5,728,732, the contents of which are incorporated herein. Further, it is not known that salicylic acid can be used in combination with the other components of the present invention to treat rosacea with substantially less irritation than is normally experienced with rosacea treatment regimens. The salicylate is present in an amount of about 0.1 to 5.0 percent, preferably, 0.1 to 1.0 percent by weight of the composition.

Hinokitiol, 2-hydroxy-4-(1-methylethyl)-2,4,6-cycloheptatrien-1-one isopropyltropolone is a wood extract obtainable from for example, pine or cedar. This material is known to have potent antimicrobial effects, and, as such, has been previously used for a variety of purposes. As shown in U.S. Pat. No. 5,811,114, the contents of which are incorporated herein by reference, hinokitiol also possesses an anti-irritancy effect. The amount of hinokitiol useful in the present invention is about 0.01 to 0.5 percent, and preferably 0.1 to about 0.2 percent by weight of the composition.

The antioxidant component of the present invention prevents the harmful effects caused by reactive oxygen species or oxidants on the health of the skin and some antioxidants act as an anti-inflammatory agent. In the present invention, the antioxidant component preferably comprises at least green tea which contains volatile oil, vitamins, minerals, caffeine and the active ingredient polyphenol. The polyphenol is a catechin, epigallocatechin gallate (EGCG) and is also believed to have antibacterial properties. The polyphenol is also known as an antioxidant. The incorporation of an antioxidant in a composition for treating rosacea is disclosed in U.S. Pat. No. 5,972,993, and green tea and a sunscreen, including a salicylate, is disclosed in U.S. Pat. No. 5,306,486, the contents of which are incorporated herein. Other known antioxidants can be used such as, for example, but not limited to, vitamins such as vitamin C and vitamin E, BHT, extracts from various plants, such as for example, rosemary. The green tea is present in an amount of about 0.1 to 0.5 percent by weight of the composition.

The anti-irritant component of the present invention comprises at least a polysaccharide and gorgonian extract. The extracts of gorgonian are also known to have antimicrobial activity as reported by Jensen, P. R., et al., "Antimicrobial activity of extracts of Caribbean gorgonian corals", Marine Biology, vol. 125, pp. 411 to 419 (1996). Caribbean gorgonians (*Octocorallia gorgonacea, Phylum cnidaria*) are a diverse group of marine animals which are commonly known as sea whips and sea fans. Upon analysis of the Caribbean gorgonian, it has been found that they are or can be a biologically active source of pseudopterosin, steroids, prostaglandins, lactones, sesquiterpenoid derivatives, and diterpenoid metabolites, such as, for example, diterpenoid glycosides. As described in U.S. Pat. No. 5,624,911, ether derivatives of pseudopterosin, derived from marine sea whip, are effective anti-inflammatory and analgesic agents. Gorgonian extract is available commercially from Centerchem, Stamford, Conn. The gorgonian extract is present in an amount of about 0.01 to 0.5 percent, preferably 0.05 to 0.2 percent by weight of the composition.

Although any polysaccharide can be used in the compositions of the present invention, the polysaccharide of the present invention is preferably an extract of red algae, of the species, Porphyridium. The polysaccharide is commercially available from Earth Salts Company. As described in U.S. Pat. No. 5,089,481 and International Patent Application WO 97/00689, the red algae polysaccharide is chemically composed of mostly xylose, glucose, and galactose. Both of these references are incorporated herein by reference. In particular, the red algae polysaccharide contains, in addition to galactose, a dimethyl galactose. As the algae grow in a liquid medium, polysaccharide is released from the cell surface. Thus, polysaccharide can be collected from the excretions of algae in a growth medium or, alternatively, it can be obtained from the cell walls by extraction. It has been known that algal polysaccharides inhibit the activity of viruses such as human immunodeficiency virus reverse transcriptase enzyme and herpes simplex virus. However, the ability of these polysaccharides to reduce irritation associated with the rosacea condition has not previously been described. Specifically, it has not been known to incorporate the red microalgae polysaccharide of the present invention in combination with the other anti-irritants in the anti-irritant component to treat rosacea without substantial irritation. The polysaccharide is present in an amount of about 0.5 to 2.0 percent by weight of the composition.

While not so limited, in a preferred embodiment, the emulsion of the invention is an oil-in-water emulsion. The aqueous phase may be any cosmetically acceptable water based material, such as deionized water, or a floral water. The oil phase may be any cosmetically or pharmaceutically acceptable oil, such an oil being defined for the present purpose as any pharmaceutically or cosmetically acceptable material which is substantially insoluble in water. The oils may be volatile or non-volatile, or a mixture of both. For example, suitable volatile oils include, but are not limited to, both cyclic and linear silicones, such as cyclomethicone, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, di- or triglycerides, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum.

The emulsions may also comprise other optional components, depending on the intended end use. These include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like. However, any additional optional component must not interfere with the reduction in irritation and the anti-angiogenesis activity achieved by the components of the present invention.

The invention is further illustrated by the following non-limiting examples.

EXAMPLES

Example I

| Ingredient | Percent |
| --- | --- |
| Phase I | |
| Deionized Water | 64.40 |
| Methyl Paraben | 0.10 |
| Sodium Hinokitiol | 0.15 |
| Phenoxyethanol | 0.10 |
| Phase II | |
| Hyaluronic Acid | 0.10 |
| Methylcellulose | 0.50 |
| Phase III | |
| Deionized Water | 12.15 |
| Salicylic Acid | 0.50 |
| Phase IV | |
| Phytosphingosine | 0.20 |
| Dimethicone | 5.00 |
| Cyclomethicone | 15.00 |
| Green Tea | 0.40 |
| Gorgonian Extract | 0.20 |
| Polysaccharide | 1.10 |
| Fragrance | 0.10 |

A composition according to the present invention is prepared as follows:

To prepare the composition, combine the Phase I ingredients. Add the Phase II ingredients to the Phase I ingredients when they are clear and uniform. Premix Phase II ingredients and combine with the Phases I and II ingredients. Add Phase IV ingredients to the combined Phases I, II and III.

Example II

A composition according to the present invention, as similarly provided in Example 1, is tested to determine its effect on reducing the signs of rosacea, and in particular, the redness associated with telangiectasia. The study includes 18 female participants between the ages of 18 and 50. The participants have skin type I–II and are considered to have skin that is flushed or blushed. Therefore, the participants exhibit mild to moderate rosacea, and in particular, the redness associated with rosacea due to the flushing/blushing. The participants do not show signs of excessive acne associated with rosacea and are considered to be in normal health without signs or evidence of acute or chronic disease including dermatologic or ophthalmologic problems other than mild to moderate rosacea. Participants do not exhibit current sunburn, rashes, scratches, or burn marks because these skin conditions might interfere with the evaluation of test results. In addition, the study excludes as participants any female that is pregnant or lactating.

Besides the compositions of the study, the participants are instructed to refrain from using systemic or topical retinoids, antihistamines, or other similar agents during the course of the study. In addition, the participants are instructed to use the compositions of the present invention on the full face two times a day for one month. During the period of the study, the participants continue to use the cleansers and cover makeup that they normally use and agree not to change brands during the study. The participants do not use any other topical moisturizers during the study.

The study is blinded (i.e., the participants are unaware of the nature of the materials being tested) and lasts for four months of using the product. The participants apply the compositions of the present invention two times a day, morning and evening, and apply a moisturizing composition containing retinol at night. Participants appear for testing without any facial makeup or treatment products. Thus, on the day of testing, the participants do not use the product for at least 12 hours before measurements are taken. The participants keep a daily diary which is monitored and participants return the package containing the composition of the present invention for assessment of the remaining package content at the conclusion of the study.

Measurements are taken as baseline, and after one, two, three, and four months of product use. The blood flow in facial skin of the participants is measured using a Laser Doppler Capillary perfusion Monitor and photographs are obtained using digital photographic equipment. At the conclusion of the study, the participants complete a questionnaire to determine their assessment of the efficacy of the compositions of the present invention. The results of percent reduction of blood flow in facial skin is illustrated in FIG. 1 wherein it is shown that blood flow is reduced over a period of four months between 14 percent and 26 percent for 16 out of the 18 participants. Two of the 18 participants experienced irritation. The greatest reduction of 26 percent is achieved after four months, and therefore, indicates that the compositions of the present invention are effective in reducing the blood flow to the facial skin. The study demonstrates the redness associated with telangiectasia is reduced. In addition, all of the 16 participants experienced either a reduction in the feeling of sensitivity in their skin or no change. With respect to dry skin sensitivity, 6 participants reported that their skin was less dry after using the compositions of the present invention. These results demonstrate that the compositions of the present invention for treating rosacea are effective and substantially non-irritating.

What we claim is:

1. A topical cosmetic or pharmaceutical composition for skin treated with a retinoid for a condition of rosacea, comprising a combination of a phytosphingosine;

an antioxidant component; comprising at least a green tea an anti-bacterial component comprising at least hinokitiol and a salicylate; and an anti-irritating component comprising at least a polysaccharide and gorgonian extract.

2. The composition of claim 1 further wherein the composition comprises about 0.01 to 10.0 percent of the phytosphingosine, about 0.1 to 0.5 percent of the antioxidant component comprising at least a green tea, about 0.05 to 0.2 percent of the hinokitiol, about 0.1 to 5.0 percent of the salicylate, about 0.05 to 0.2 percent of the gorgonian extract, and about 0.5 to 2.0 percent of the polysaccharide.

3. The composition of claim 2 in which the salicylate is selected from the group consisting of salicylic acid and salicylic acid ester.

4. The composition of claim 1 which comprises said salicylate in an amount of from about 0.2 to 1.0 percent by weight of the total composition.

5. A method of treating telangiectasis comprising topically applying to the skin the compositions of claim 1.

6. A method of treating rosacea comprising topically applying to the skin the compositions of claim 1.

7. A topical cosmetic or pharmaceutical composition for treating the telangiectasic symptom of rosacea on skin treated with a retinoid comprising a combination of a) about 0.01 to 10.0 percent phytosphingosine, b) an effective amount of a combination of an antioxidant component comprising at least about 0.1 to 0.5 percent green tea, c) an anti-bacterial component comprising at least about 0.05 to 0.2 percent hinokitiol and about 0.1 to 5.0 percent salicylate, and d) an anti-irritant component comprising a combination of about 0.05 to 0.2 percent gorgonian extract and about 0.5 to 2.0 percent polysaccharide.

8. A rosacea treatment system for topical application to skin treated with a retinoid comprising a) an anti-bacterial component comprising about 0.1 to 5.0 percent of a salicylic acid and about 0.05 to 0.2 percent hinokitiol, b) about 0.01 to 10.0 percent phytosphingosine, c) an effective amount of an antioxidant component comprising at least about 0.1 to 0.5 percent green tea, and d) an anti-irritating component comprising a combination of about 0.05 to 0.2 percent gorgonian extract, and about 0.5 to 2.0 percent polysaccharide.

9. A method of decreasing irritation on skin for a condition of rosacea which comprises topically applying to skin treated with a retinoid, a composition comprising a salicylate, a phytosphingosine, and an anti-irritating component comprising a mixture of a green tea, a hinokitiol, a gorgonian extract, and a polysaceharide.

10. A method of decreasing redness on skin for a condition of rosacea comprising topically applying to the skin topically treated with a retinoid a composition comprising a phytosphingosine, a salicylate, and a mixture of an antioxidant component comprising at least a green tea, an anti-bacterial component comprising at least a hinokitiol, an anti-irritating component comprising a mixture of a gorgonian extract and a polysaccharide.

* * * * *